US007229460B2

(12) United States Patent
Kramer

(10) Patent No.: US 7,229,460 B2
(45) Date of Patent: *Jun. 12, 2007

(54) CATHETER SYSTEM WITH CATHETER AND GUIDEWIRE EXCHANGE

(75) Inventor: Barry L. Kramer, Chicago, IL (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 392 days.

This patent is subject to a terminal disclaimer.

(21) Appl. No.: 10/737,704

(22) Filed: Dec. 16, 2003

(65) Prior Publication Data
US 2004/0176793 A1 Sep. 9, 2004

Related U.S. Application Data

(63) Continuation of application No. 07/881,673, filed on May 12, 1992, now Pat. No. 6,685,721, which is a continuation of application No. 07/713,973, filed on Jun. 11, 1991, now Pat. No. 5,135,535.

(51) Int. Cl.
A61M 29/00 (2006.01)
A61M 5/178 (2006.01)

(52) U.S. Cl. .................. 606/194; 604/102.02; 604/160

(58) Field of Classification Search ................ 604/102, 604/96, 160, 161, 282; 606/192, 195, 194
See application file for complete search history.

(56) References Cited

U.S. PATENT DOCUMENTS

| 3,262,449 | A | 7/1966  | Pannier et al. |
| 3,297,030 | A | 1/1967  | Czorny et al. |
| 3,545,443 | A | 12/1970 | Ansari |
| 3,550,591 | A | 12/1970 | MacGregor |
| 3,603,311 | A | 9/1971  | Huggins |
| 3,682,173 | A | 8/1972  | Center |
| 3,853,130 | A | 12/1974 | Sheridan |
| 4,037,599 | A | 7/1977  | Raulerson |
| 4,054,136 | A | 10/1977 | von Zeppelin |
| 4,079,738 | A | 3/1978  | Dunn et al. |
| 4,147,165 | A | 4/1979  | Tauschinski |
| 4,175,564 | A | 11/1979 | Kwak |
| 4,323,071 | A | 4/1982  | Simpson et al. |

(Continued)

FOREIGN PATENT DOCUMENTS

EP 0282143 A1 9/1888

(Continued)

Primary Examiner—Gary E. O'Connor
(74) Attorney, Agent, or Firm—McAndrews Held & Malloy, Ltd.

(57) ABSTRACT

An intravascular catheter system, such as a dilatation catheter system for angioplasty procedures, which provides for the replacement of the catheter or the guidewire during the procedure. The intravascular catheter has a guidewire-receiving inner lumen extending along its length. A first guidewire port is provided in the catheter body at or near the proximal end of the catheter. A second guidewire port is provided in the catheter body at a location spaced distally from the first guidewire port and proximally from a diagnostic or therapeutic tool, such as a dilatation balloon, on a distal portion of the catheter. A third guidewire port is provided in the distal end of the catheter. The guidewire ports are in communication with the guidewire-receiving inner lumen.

1 Claim, 2 Drawing Sheets

U.S. PATENT DOCUMENTS

| | | | |
|---|---|---|---|
| 4,411,055 A | 10/1983 | Simpson et al. | |
| 4,411,654 A | 10/1983 | Boarini et al. | |
| 4,439,185 A | 3/1984 | Lundquist | |
| 4,468,224 A | 8/1984 | Enzmann et al. | |
| RE31,855 E | 3/1985 | Osborne | |
| 4,516,972 A | 5/1985 | Samson | |
| 4,538,622 A | 9/1985 | Samson et al. | |
| 4,554,929 A | 11/1985 | Samson et al. | |
| 4,569,347 A | 2/1986 | Frisbie | |
| 4,573,470 A | 3/1986 | Samson et al. | |
| 4,581,017 A | 4/1986 | Sahota | |
| 4,582,181 A | 4/1986 | Samson | |
| 4,585,013 A | 4/1986 | Harris | |
| 4,596,559 A | 6/1986 | Fleischhacker | |
| 4,616,652 A | 10/1986 | Simpson | |
| 4,619,644 A | 10/1986 | Scott | |
| 4,631,056 A | 12/1986 | Dye | |
| 4,631,059 A | 12/1986 | Wolvek et al. | |
| 4,638,805 A | 1/1987 | Powell | |
| 4,705,507 A | 11/1987 | Boyles | |
| 4,723,948 A | 2/1988 | Clark et al. | |
| 4,738,666 A | 4/1988 | Fuqua | |
| 4,747,833 A | 5/1988 | Kousai et al. | |
| 4,748,982 A | 6/1988 | Horzewski et al. | |
| 4,748,986 A | 6/1988 | Morrison et al. | |
| 4,762,129 A | 8/1988 | Bonzel | |
| 4,771,777 A | 9/1988 | Horzewski et al. | |
| 4,813,930 A | 3/1989 | Elliott | |
| 4,821,722 A | 4/1989 | Miller et al. | |
| 4,865,593 A | 9/1989 | Ogawa et al. | |
| 4,883,468 A | 11/1989 | Kousai et al. | |
| 4,888,000 A | 12/1989 | McQuilkin et al. | |
| 4,898,577 A | 2/1990 | Badger et al. | |
| 4,931,049 A | 6/1990 | Klimas | |
| 4,944,745 A | 7/1990 | Sogard | |
| 4,947,864 A | 8/1990 | Shockey et al. | |
| 4,981,478 A | 1/1991 | Evard et al. | |
| 4,988,356 A | 1/1991 | Crittenden et al. | |
| 4,997,424 A | 3/1991 | Little | |
| 5,024,234 A | 6/1991 | Leary et al. | |
| 5,034,001 A | 7/1991 | Garrison et al. | |
| 5,046,503 A | 9/1991 | Schneiderman | |
| 5,061,267 A | 10/1991 | Zeiher | |
| 5,061,273 A | 10/1991 | Yock | |
| 5,102,403 A | 4/1992 | Alt | |
| 5,135,482 A | 8/1992 | Neracher | |
| 5,154,725 A | 10/1992 | Leopold | |
| 5,171,222 A | 12/1992 | Euteneuer et al. | |
| 5,195,978 A | 3/1993 | Schiffer | |
| 5,205,822 A | 4/1993 | Johnson et al. | |
| 5,267,982 A | 12/1993 | Sylvanowicz | |
| 5,395,335 A | 3/1995 | Jang | |

FOREIGN PATENT DOCUMENTS

| | | |
|---|---|---|
| EP | 0274129 A2 | 7/1988 |
| EP | 0388112 A2 | 9/1990 |
| EP | 0416662 B1 | 3/1991 |
| WO | WO 82/03558 | 10/1982 |
| WO | WO 91/05512 | 5/1991 |
| WO | WO 92/17236 | 10/1992 |
| WO | WO 92/20397 | 11/1992 |
| WO | WO 92/22345 | 12/1992 |

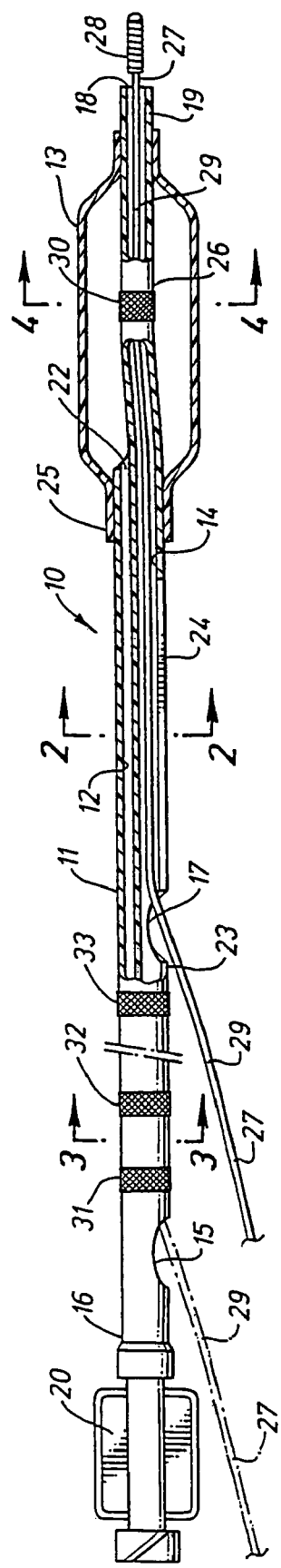
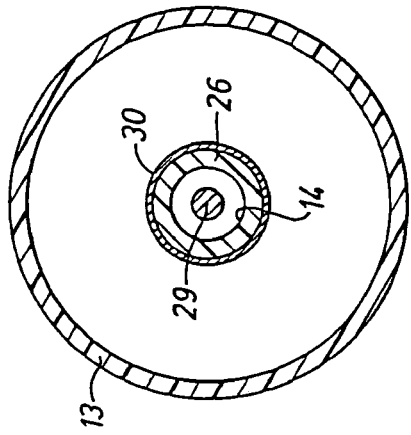
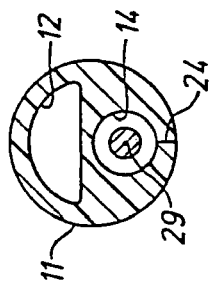
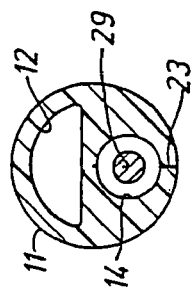

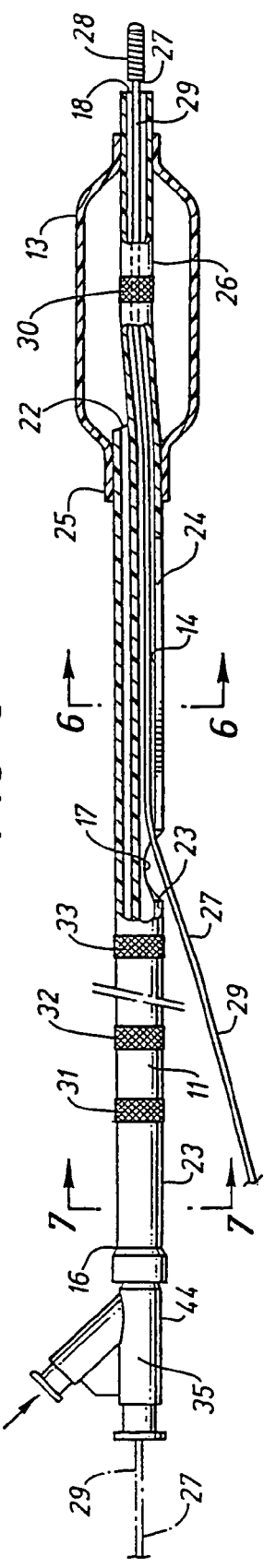
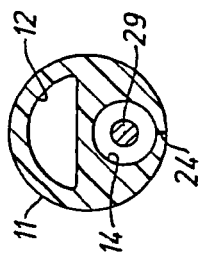

CATHETER SYSTEM WITH CATHETER AND GUIDEWIRE EXCHANGE

RELATED APPLICATIONS

This application is a continuation of application Ser. No. 07/881,673, filed May 12, 1992, now U.S. Pat. No. 6,685,721 which is a continuation of application Ser. No. 07/713,973, filed Jun. 11, 1991, now U.S. Pat. No. 5,135,535. The disclosures of the above-identified patent applications and the above-identified Patent are hereby incorporated by reference in their entirety.

BACKGROUND OF THE INVENTION

This invention generally relates to a catheter system which is suitable for intravascular procedures such as percutaneous transluminal coronary angioplasty (PTCA) and which allows for the exchange of guidewires and catheters during such procedures.

In classic PTCA procedures, a guiding catheter having a preshaped distal tip is percutaneously introduced into the cardiovascular system of a patient. The guiding catheter is advanced until its preshaped distal tip is disposed within the aorta adjacent the ostium of the desired coronary artery. The guiding catheter is twisted or torqued from the proximal end to turn the distal tip of the guiding catheter, so it can be guided into the coronary ostium.

A dilatation catheter having a balloon on its distal end and a guidewire slidably disposed within an inner lumen of the dilatation catheter are introduced into and advanced through the guiding catheter to its distal tip. The distal tip of the guidewire is usually manually shaped (i.e. curved) by the physician or one of the attendants before the guidewire is introduced into the guiding catheter along with the dilatation catheter.

The guidewire is first advanced out the distal tip of the guiding catheter, which is seated in the ostium of the patient's coronary artery, into the patient's coronary artery. A torque is applied to the proximal end of the guidewire, which extends out of the patient, to guide the curved or otherwise shaped distal end of the guidewire as the guidewire is advanced within the coronary anatomy until the shaped distal end of the guidewire enters the desired artery. The advancement of the guidewire within the selected artery continues until it crosses the lesion to be dilated.

The dilatation catheter is then advanced out of the distal tip of the guiding catheter, over the previously advanced guidewire, until the balloon on the distal extremity of the dilatation catheter is properly positioned across the lesion. Once properly positioned, the flexible, relatively inelastic balloon is inflated to a predetermined size with radiopaque liquid at relatively high pressures (e.g., 4–12 atmospheres) to dilate the stenosed region of the diseased artery. The balloon is then deflated, so the dilatation catheter can be removed from the dilated stenosis and blood flow can then be resumed.

Further details of guiding catheters, dilatation catheters, guidewires, and the like for angioplasty procedures can be found in U.S. Pat. No. 4,323,071 (Simpson-Robert); U.S. Pat. No. 4,439,185 (Lundquist); U.S. Pat. No. 4,468,224 (Enzmann et al.); U.S. Pat. No. 4,516,972 (Samson); U.S. Pat. No. 4,438,622 (Samson et al.); U.S. Pat. No. 4,554,929 (Samson et al.); U.S. Pat. No. 4,582,185 (Samson); U.S. Pat. No. 4,616,652 (Simpson); U.S. Pat. No. 4,638,805 (Powell); U.S. Pat. No. 4,748,986 (Morrison et al.); U.S. Pat. No. 4,898,577 (Badger et al.); and U.S. Pat. No. 4,748,982 (Horzewski et al.) which are incorporated by reference.

Recently, Advanced Cardiovascular Systems, Inc., introduced into the marketplace an improved dilatation catheter which is described and claimed in copending application Ser. No. 07/550,801 (Yock), filed Jul. 9, 1990 and U.S. Pat. No. 4,748,982 (Horzewski et al.). This dilatation catheter has a short guidewire-receiving sleeve or inner lumen extending through just the distal portion of the catheter. The sleeve extends proximally at least 10 cm, typically about 25 cm, from a guidewire port in the distal end of the catheter to another guidewire port in the wall of the catheter. A slit is provided in the catheter wall. The slit extends distally from the second guidewire port to a location proximal to the proximal end of the inflatable balloon. The structure of the catheter allows for the rapid exchange of the catheter without the need for an exchange wire or adding a guidewire extension to the proximal end of the guidewire.

The catheter design embodying the Yock and Horzewski et al. improvements has been widely praised by members of the medical profession and has met with much commercial success in the market place. Nonetheless, there are some inconveniences in its use because the catheter does not allow for the exchange or replacement of the guidewire. For example, the shaped distal tip of the guidewire may become deformed in use or the shape of the distal tip or the size of the guidewire may be found to be no longer suitable for the particular procedure within the patient's vasculature. In this instance the physician might want to remove the guidewire and reshape the distal tip or replace the first guidewire with another having the desired size, stiffness or shape.

When the guidewire in a dilatation catheter system embodying the Yock and Horzewski et al. improvements is removed, however, access to the desired arterial location through the distal guidewire lumen of the catheter is lost. Unfortunately, there is no way to clinically determine before the guidewire is inserted into the patient in an angioplasty procedure whether a guidewire or a catheter will have to be exchanged during the procedure.

BRIEF SUMMARY OF THE INVENTION

What has been needed and heretofore unavailable is an intravascular catheter system which allows for the rapid exchange of either the catheter or the guidewire during an intravascular procedure without losing access to the desired region of the patient's arterial system. The present invention satisfies this and other needs.

The present invention is an elongated catheter for performing an intravascular procedure within a patient's vascular system. This catheter system can be used in an over-the-wire type mode and can also allow for the exchange of either a guidewire or a catheter mounted over a guidewire during an intraluminal procedure without losing access to the body lumen. One example of an interluminal procedure for which this catheter is particularly useful is percutaneous coronary angioplasty (PTCA).

The catheter includes an elongated catheter body having proximal and distal ends and an exterior. A guidewire-receiving inner lumen extends within the catheter body to its distal end. Means are provided on the distal portion of the catheter body for performing an intravascular procedure. The means may take the form of any known tool, such as a dilatation balloon.

A first guidewire port is provided in the catheter body at or near the proximal end of the catheter body. The first guidewire port is in communication with the guidewire-receiving inner lumen.

A second guidewire port is provided in the catheter body. The second guidewire port is spaced proximally from the tool to perform a vascular procedure and a short distance from the distal end of the catheter body. The second guidewire port is in communication with the guidewire-receiving inner lumen.

A third guidewire port is provided in the distal end of the catheter body. The third guidewire port is in communication with the guidewire-receiving inner lumen.

A wall portion of the catheter body at least partially defines the guidewire receiving inner lumen. The wall portion is openable substantially from the first guidewire port substantially to the second guidewire port, and from the guidewire-receiving inner lumen to the exterior of the catheter body. The wall of the catheter body opens to allow a guidewire to exit laterally from the inner lumen through the wall portion by peeling the catheter body from the guidewire.

In a presently preferred embodiment the catheter is a balloon dilatation catheter adapted to perform PTCA procedures. One of the attractive features of this catheter design is that the catheter can be used as an over-the-wire type dilatation catheter in a conventional fashion, yet it allows both the catheter and the guidewire to be exchanged during the PTCA procedure. Similar catheter designs can be used with other intraluminal catheters that have diagnostic or therapeutic tools on the distal portion of the catheter.

BRIEF DESCRIPTION OF SEVERAL VIEWS OF THE DRAWINGS

FIG. 1 is an elevational view, partially in section, of a dilatation catheter having a guidewire-receiving inner lumen that embodies features of the invention.

FIG. 2 is a transverse, cross-sectional view of the catheter shown in FIG. 1 taken along the lines 2—2.

FIG. 3 is a transverse, cross-sectional view of the catheter shown in FIG. 1 taken along the lines 3—3.

FIG. 4 is a transverse, cross-sectional view of the catheter shown is FIG. 1 taken along the lines 4—4.

FIG. 5 illustrates an alternate embodiment of the invention in which a guidewire extends out the proximal end of an adapter mounted on the proximal end of the catheter body.

FIG. 6 is a transverse, cross-sectional view of the catheter shown in FIG. 5 taken along the lines 6—6.

FIG. 7 is a transverse, cross-sectional view of the catheter shown in FIG. 5 taken along the lines 7—7.

The foregoing summary, as well as the following detailed description of the preferred embodiments of the present invention, will be better understood when read in conjunction with the appended drawings. For the purpose of illustrating the preferred embodiments of the present invention, there is shown in the drawings, embodiments which are presently preferred. It should be understood, however, that the present invention is not limited to the arrangements and instrumentality shown in the attached drawings.

DETAILED DESCRIPTION OF THE INVENTION

While the invention will be described in connection with one or more embodiments, it will be understood that the invention is not limited to those embodiments. On the contrary, the invention includes all alternatives, modifications, and equivalents as may be included within the spirit and scope of the appended claims.

FIGS. 1–4 illustrate a dilatation catheter 10 embodying features of the invention. The catheter 10 allows for the exchange of a guidewire while the catheter remains in place within the patient and which also allow for the exchange of the catheter while the guidewire remains in place so as to avoid loss of the arterial position. The catheter 10 generally comprises an elongated catheter body 11 and a guidewire-receiving inner lumen 14 extending therein. An inflation lumen 12 is adapted to direct inflation fluid from the proximal end of the catheter body to the interior of an inflatable balloon 13 or other diagnostic or therapeutic components on the distal portion of the catheter body.

The catheter body 11 has a wall defining at least part of the guidewire-receiving inner lumen 14. The body 11 has a first guidewire port 15 near the proximal end 16 of the catheter body. The body 11 has a second guidewire port 17 distal to the first port and at least about 10 cm from the distal end of the catheter body. The body 11 has a third guidewire port 18 located in the distal end 1a of the catheter body. The second guidewire port 17 is substantially closer to the third port 18 than the first port 15.

The first guidewire port 15 is generally at or close to the proximal end of the catheter body 11, e.g. usually not more than about 30 cm away, and, preferably, is not more than about 10 cm from the proximal end of the catheter body 11. The second port 17 is spaced closer to the diagnostic or therapeutic tool than it is to the first port 15 and generally is at least about 10 cm from the distal end of the catheter body preferably about 15 cm to about 40 cm.

An adapter 20 is provided on the proximal end 16 of the catheter body 11 to facilitate the introduction of inflation fluid into the inflation lumen 12 which directs the fluid to the interior of the inflatable balloon 13 through the inflation port 22.

A first slit 23 is preferably provided in the wall of the catheter body which defines the guidewire-receiving inner lumen 14 and extends between the first guidewire port 15 and the second guidewire port 17. A second slit 24 is provided in the wall of the catheter body 11 which further defines the guidewire-receiving inner lumen and extends from the second guidewire port 17 to a location proximal to the proximal end 25 of the balloon 13.

The catheter body 11 has a tubular extension 26 on its distal portion that extends through the interior and out the distal end of the balloon 13. The tubular extension 26 is adapted to receive a guidewire 27 within the inner lumen 14. The guidewire 27 has a coil 28 on its distal end which is shown extending out the third guidewire port 18 in the distal end 19 of the catheter body 11. The guidewire 27 has an elongated core member 29 that is shown extending out the second guidewire port 18. The guidewire 27 is shown in phantom in a second position disposed within the proximal section of the inner lumen 14. The proximal portion of the elongated core member 29 extends out the first guidewire port 15 near the proximal end 16 of the catheter body 11.

A radiopaque marker 30 is disposed about the tubular extension 26 within the interior of the balloon 13 to facilitate fluoroscopic observation during an intravascular procedure. Radiopaque markers 31, 32 and 33 may also be provided on the proximal portion of the catheter body 11 to allow the physician to fluoroscopically determine the location of the first and second guidewire ports and the like during the intravascular procedures.

The catheter system of the invention can be inserted into the patient in a conventional over-the-wire fashion with the guidewire 27 preloaded within the inner lumen 14 and extending proximally out the first or proximal port 15. Alternatively, the catheter can be inserted in a manner similar to that used to insert catheters having the improvements of Yock and Horzewski et al. wherein the guidewire extends proximally out the second or intermediate guidewire port 17. It sometimes is desirable or necessary during the intravascular procedure to remove or replace either the catheter 10 or the guidewire 27. Either may be removed by pulling on the proximal end (that extends out of the patient) while the catheter or guidewire which remains within the patient is held in position in order to maintain access to the desired intravascular location.

If the guidewire is to be removed, the catheter 10 is held in place while the guidewire is pulled out of the proximal end of the guiding catheter and the catheter 10. When the guidewire has been removed from the catheter 10, a replacement guidewire may then be inserted through the first guidewire port 15, which is outside the patient. The guidewire is inserted into the inner lumen 14 and advanced until the guidewire exits the third guidewire port 18 in the distal end 19 of the catheter body 11 into the patient's coronary artery. Once the replacement guidewire 27 is properly positioned within the patient's artery, e.g. across a stenosis to be dilated, the dilatation catheter 10 may then be further advanced within the artery over the replacement guidewire. The catheter is advanced to the desired location to perform the dilatation or other diagnostic or therapeutic procedure in a conventional manner.

If the catheter 10 is to be removed and the guidewire 27 extends proximally out the first guidewire port 15, the guidewire and the catheter are separated while the catheter is being removed by peeling the catheter body 10 laterally from the guidewire while maintaining the guidewire essentially motionless. The site of peeling is outside the patient's body. The peeling process continues until the guidewire extends out the second guidewire port 17. The peeling of the catheter is continued by holding the guidewire 27 still and peeling the catheter body laterally away to pass the guidewire 27 through the slit 24 while the catheter is being withdrawn.

When the distal end 19 of the catheter exits the proximal end of the guiding catheter, the guidewire may be manually gripped distal of the distal end 19, and the catheter 10 may be removed from the proximal end of the guidewire. If the guidewire 27 exits the second guidewire port 17, the procedure is essentially the same, except that there is no need to peel the catheter 10 away from the guidewire through the slit 23 proximally of the second guidewire port 17.

When the catheter 10 has been removed, a replacement catheter is mounted onto the guidewire 27. This can be done by inserting the proximal end of the guidewire 27 through the third guidewire port 18 in the distal end 19 of the replacement catheter and advancing the catheter 10 over the guidewire 27 disposed within the inner lumen 14 of the catheter. The catheter 10 is advanced until the guidewire 27 exits the second guidewire port 17. The replacement catheter may then be inserted into the patient and advanced in a conventional manner as described in the previously-cited Yock application or Horzewski et al. patent which are incorporated here by reference.

In another method the replacement catheter is mounted onto the guidewire 27 as previously described but the replacement catheter is advanced over the guidewire 27 until the proximal end of the guidewire 27 exits the first guidewire port 15. In this method the replacement catheter is advanced well within the patient's vasculature before the proximal end of the guidewire exits the first port. The guidewire is manually grasped and the replacement catheter advanced further over the wire into the patient's coronary arteries.

An alternate embodiment of the invention is illustrated in FIGS. 5–7. This embodiment is quite similar to the embodiment shown is FIGS. 1–4 except that the guidewire 27 extends through the center arm of the two arm adapter 35 on the proximal end of the catheter body 11. The corresponding parts of this embodiment are numbered the same as the parts of the embodiments shown in FIGS. 1–4.

The first guidewire port 15 in this embodiment (not shown in the drawings) is in the proximal end 16 of the catheter body 11 and opens to the adapter 35. The use of this embodiment is essentially the same as the embodiment shown in FIGS. 1–4. The adapter 35 is modified to include a slit 44 that is continuous with the slit 23 in the catheter body 11.

The catheter body 11 can be formed by conventional techniques, e.g. extruding, from materials already found useful in intravascular catheters such polyethylene, polyimide, polyvinyl chloride, polyester, or composite materials. Some composite materials are described in U.S. Pat. No. 4,981,478 (Evard et al.) which is incorporated here by reference. The various components of the catheter can be joined by suitable adhesive such as the acrylonitrile-based adhesive sold as Loctite.™ 405. Heat shrinking may also be employed where appropriate. A venting means (i.e. a vent) may be provided to remove air from the interior of the balloon before the catheter is inserted into the patient such as described in U.S. Pat. No. 4,638,805 (Powell) and U.S. Pat. No. 4,821,722 (Samson et al.) which are incorporated here by reference.

The size of the catheter body 11 and the guidewire-receiving inner lumen 14 to a large extent are determined by the size of the guidewires 27 to be employed and the size of the artery or other body lumen through which the catheter must pass. Generally, the diameter of the inner lumen is sufficient to accommodate the guidewire and to allow it to be slidably disposed therein. The diameters of guidewires for coronary use can vary. They may be from about 0.008 to about 0.035 inch (0.2–0.89 mm) in diameter. The inner diameter of the guidewire-receiving inner lumen 14 of the catheter 10 should be about 0.001 to about 0.005 inch (0.025–0.127 mm) larger than the diameter of the guidewire.

The catheter body 11 is sufficiently long to extend from outside the proximal end of a guiding catheter, which likewise extends out of the patient, to a stenosis to be treated within the patient's vascular system (or other desired location therein). The length of the catheter may be from about 100 to about 150 cm when a Seldinger approach through the femoral artery is employed to introduce the catheter 10 into the patient's vasculature. The wall forming the catheter must be of sufficient thickness and strength that it can be pushed over the guidewire 27 to the desired location within the patient's blood vessel. If desired the proximal portion of the dilatation catheter 10 can be provided with a stiffener to facilitate the advancement of the catheter within the patient's vasculature.

The catheter system of the invention also allows for the exchange of an in-place guidewire during an intraluminal procedure while holding the catheter in place to maintain access to the intraluminal position. To replace an in-place guidewire, it is removed from the guidewire-receiving inner lumen of the catheter and the patient by pulling on its proximal end that extends out of the patient.

When the in-place guidewire is removed from the inner lumen of the in-place catheter, the replacement guidewire is inserted into the guidewire-receiving inner lumen of the in-place catheter through the proximal guidewire port. The replacement catheter is advanced through the guidewire-receiving inner lumen and out the third port in its distal end to the desired location within the patient's body lumen. If the in-place guidewire extends out the second guidewire port, it may be desirable to have the replacement guidewire inserted into the proximal portion of the guidewire-receiving inner lumen through the first or proximal guidewire port before the in-place guidewire is removed from the distal portion of the inner lumen. If that is done, there is little chance of losing access to the site of treatment by the accidental movement of the in-place catheter. The replacement guidewire is advanced through the in-place catheter and properly positioned in a desired location therein, e.g. across a stenosis in a patient's artery which is to be dilated. The catheter may then be advanced over the replacement guidewire to the desired location to perform the desired diagnostic or therapeutic treatment therein.

The intravascular catheter of the invention also allows for the removal and reinsertion of a guidewire, for example, when the physician wishes to change the shape of the distal end of a guidewire during a procedure. In this operative modality, the in-place guidewire can be withdrawn in essentially the manner described above and its distal tip can be reshaped. Then the guidewire can be reintroduced into the in-place catheter in essentially the same manner as described above.

The intravascular catheter system of the invention allows for a wide variety of intravascular procedures that were heretofore impossible to perform with a single catheter system. These and other advantages are described in the following detailed description when taken in conjunction with the accompanying exemplary drawings.

While the invention has been described herein in terms of certain presently preferred embodiments directed to balloon dilatation catheters for use in coronary angioplasty procedures, those skilled in the art will recognize that the catheter of the invention may be used in a variety of body lumens. For example, the invention can be utilized in a wide variety of diagnostic and therapeutic intravascular catheters. Additionally, the catheter body may be of concentric construction rather than the dual lumen construction shown herein. Other modifications and improvements may be made to the invention without departing from the scope of the claims.

The invention claimed is:

1. An elongated catheter for performing an intravascular procedure within a patient's vascular system, comprising:
   a. an elongated catheter body having proximal and distal ends, a guidewire-receiving inner lumen extending within the catheter body to the distal end thereof;
   b. means on the distal portion of the catheter body for performing an intravascular procedure;
   c. a first guidewire port in the catheter body being at or near the proximal end of the catheter body and being in communication with the guidewire-receiving inner lumen;
   d. a second guidewire port in the catheter body being spaced proximally from the means to perform a vascular procedure and a short distance from the distal end of the catheter body and being in communication with the guidewire-receiving inner lumen;
   e. a third guidewire port in the distal end of the catheter body which is in communication with the guidewire-receiving inner lumen; and
   f. means in a wall of the catheter body defining at least in part the guidewire receiving inner lumen extending therein substantially from said first guidewire port substantially to said second guidewire port to allow a guidewire to exit laterally from the inner lumen through the wall by peeling said wall from said guidewire.

* * * * *